(12) United States Patent
Iimura

(10) Patent No.: US 6,252,081 B1
(45) Date of Patent: Jun. 26, 2001

(54) PROCESS FOR PRODUCTION OF DONEPEZIL DERIVATIVE

(75) Inventor: Yoichi Iimura, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/582,496
(22) PCT Filed: Jan. 14, 1999
(86) PCT No.: PCT/JP99/00111
§ 371 Date: Jun. 27, 2000
§ 102(e) Date: Jun. 27, 2000
(87) PCT Pub. No.: WO99/36405
PCT Pub. Date: Jul. 22, 1999

(30) Foreign Application Priority Data

Jan. 16, 1998 (JP) .................................................. 10-006908

(51) Int. Cl.⁷ ........................ C07D 213/50; C07D 211/32
(52) U.S. Cl. ........................ 546/206; 546/340; 546/343; 546/347
(58) Field of Search .................................. 546/206, 340, 546/343, 347

(56) References Cited

FOREIGN PATENT DOCUMENTS

| A1 2800919 | 7/1978 | (DE) . |
| A1 711756 | 5/1996 | (EP) . |
| 64-79151 | 3/1989 | (JP) . |
| A1 9722584 | 6/1997 | (WO) . |

OTHER PUBLICATIONS

Klingsberg, Quaternary Pyridiunium Compounds, pp. 46–51 and 86–89 (1961).
Abramovitch, Quaternary Pyridium Compunds, pp. 361–367 and 418–421 (1975).
Iriuchijima, Chemical Abstracts, vol. 114, No. 21 (1991).

Primary Examiner—Patricia L. Morris
(74) Attorney, Agent, or Firm—Birch, Stewart, Kolasch & Birch, LLP

(57) ABSTRACT

The present invention provides a novel industrially or economically preferable process for production of a hydrogen halogenide salt of a Donepezil derivative having an excellent pharmacological action as medicament, namely, reaction of 1-indanone derivative with carbonate ester to obtain 2-alkoxycarbonyl-1-indanone derivative, followed by reaction with halogenated (4-pyridyl)methyl or a salt thereof and decarboxylation successively to obtain 2-(4-pyridyl)methyl-1-indanone derivative, then reaction with halogenated benzyl to obtain quaternary ammonium salt, then reduction, and synthetic intermediates thereof.

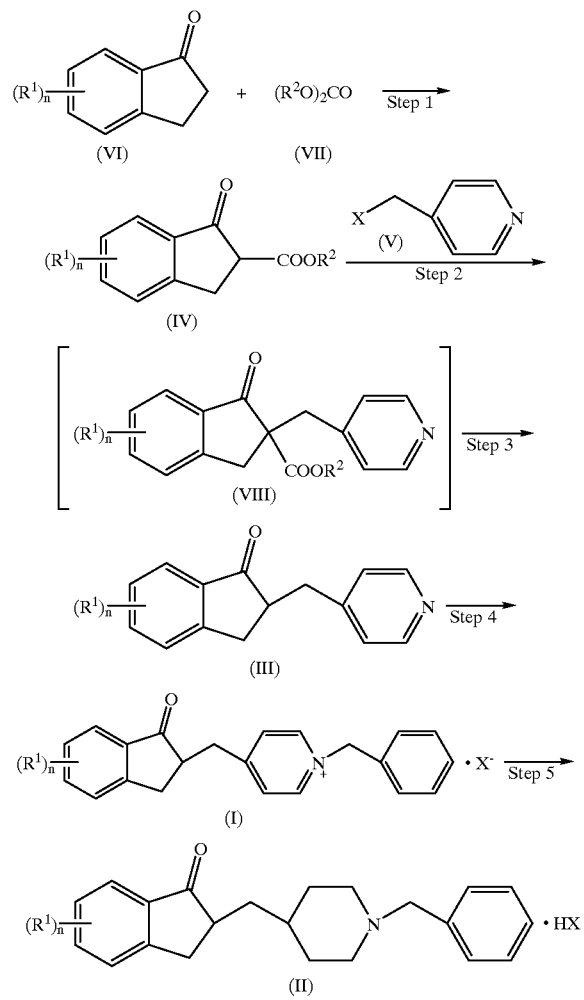

(Wherein $R^1$ represents a hydrogen atom or lower alkoxy; n represents an integer of 1 to 4; $R^2$ represents lower alkyl group; and X represents a halogen atom.)

10 Claims, No Drawings

PROCESS FOR PRODUCTION OF DONEPEZIL DERIVATIVE

This application is the national phase under 35 U.S.C. § 371 of PCT International Application No. PCT/JP99/00111 which has an International filing date of Jan. 14, 1999, which designated the United States of America.

FIELD OF THE INVENTION

The present invention relates to a novel industrial process for production of medicaments disclosed in JP-A 64-79151 (1989) (EP-296,560-A1, U.S. Pat. No. 4,895,841), specifically, Donepezil derivative having an excellent pharmacological action as prophylactic or medicament for senile dementia, especially for Alzheimer disease, and synthetic intermediates thereof. More specifically, it relates to a process for production of 1-benzyl-4-[(5,6-dimethoxy-1-indanon)-2-yl]methylpiperidine (free base) as a synthetic precursor of Donepezil Hydrochloride (chemical name; 1-benzyl-4-[(5,6-dimethoxy-1-indanon)-2-yl] methylpiperidine hydrochloride) disclosed in Example 4 of the aforementioned specification.

PRIOR ARTS

As it was disclosed in Example 3 and 4 of JP-A 64-79151 (1989), indanone derivative was produced by reacting 5,6-dimethoxy-1-indanone with 1-benzyl-4-formylpiperidine in the presence of strong base such as lithium diisopropylamide (Example 3), followed by reduction (Example 4) for example. According to this method, yield for Donepezil through Example 3 and 4 was 50.8% (62%×82%).

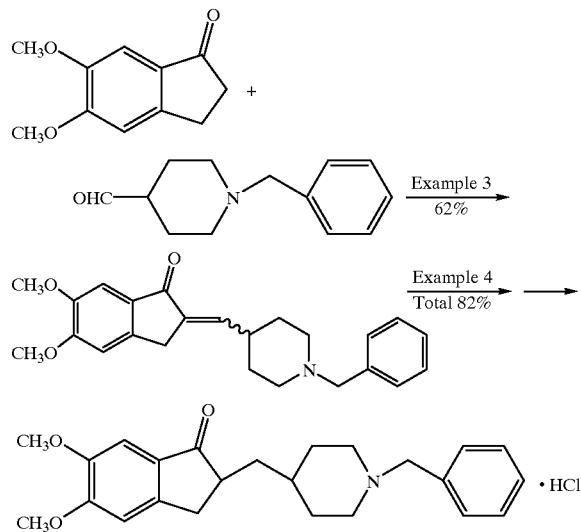

Additionally, it is disclosed in Example 2, 4 and 6 of JP-A 8-225527 (1996) (EP-711,756-A1, U.S. Pat. No. 5,606,064) that reaction of 5,6-dimethoxy-1-indanone with pyridin-4-aldehyde afforded 5,6-dimethoxy-2-(pyridin-4-yl) methyleneindan-1-one (Example 2), followed by reaction with benzyl bromide afforded 1-benzyl-4-(5,6-dimethoxyindan-1-on-2-ylidene)methylpiridinium bromide (Example 4), then reduction in the presence of platinum oxide afforded Donepezil (Example 6). According to this method, yield for Donepezil through Example 2, 4 and 6 was 58.5% (87%×83%×81%).

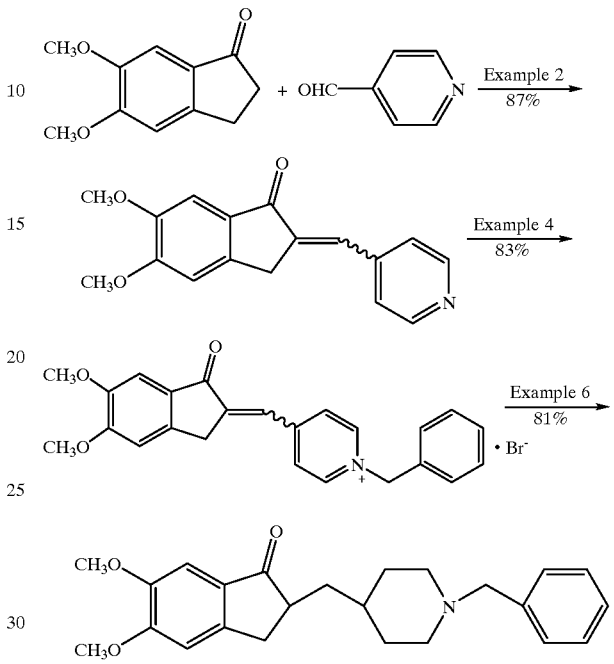

Moreover, it is disclosed in Preparation Example 1 to 3 and Example 1 to 6 of WO97/22584 that reaction of (pyridin-4-yl) carboxyaldehyde with malonic acid afforded 3-(pyridin-4-yl)-2-propenoic acid (Preparation 1), followed by reduction afforded 3-(piperidin-4-yl)-2-propionic acid (Preparation 2), followed by reaction with methyl chlorocarbonate afforded 3-[N-(methoxycarbonyl) piperidin-4-yl] propionic acid (Preparation 3), followed by reaction with oxalyl chloride afforded methyl 4-(2-chlorocarbonylethyl) piperidin-1-carboxylate (Example 1), followed by reaction with 1,2-dimethoxybenzene in the presence of aluminum chloride afforded methyl 4-[3-(3,4-dimethoxyphenyl)-3-oxopropyl]piperidin-1-carboxylate (Example 2), followed by reaction with tetramethyldiaminomethane afforded methyl 4-[2-(3,4-dimethoxybenzoyl)allyl]piperidin-1-carboxylate (Example 3), followed by treatment with sulfuric acid afforded methyl 4-(5,6-dimethoxy-1-oxoindan-2-ylmethyl) piperidin-1-carboxylate (Example 4), followed by treatment with base afforded 5,6-dimethoxy-2-(piperidin-4-ylmethyl)indan-1-one (Example 5), then reaction with benzyl bromide afforded Donepezil (Example 6).

Yield of Example 1 was not disclosed in this specification though, even it is supposed as 100%, total yield through all the steps was 19.3% (70%×84%×100%×68%×79%×61%).

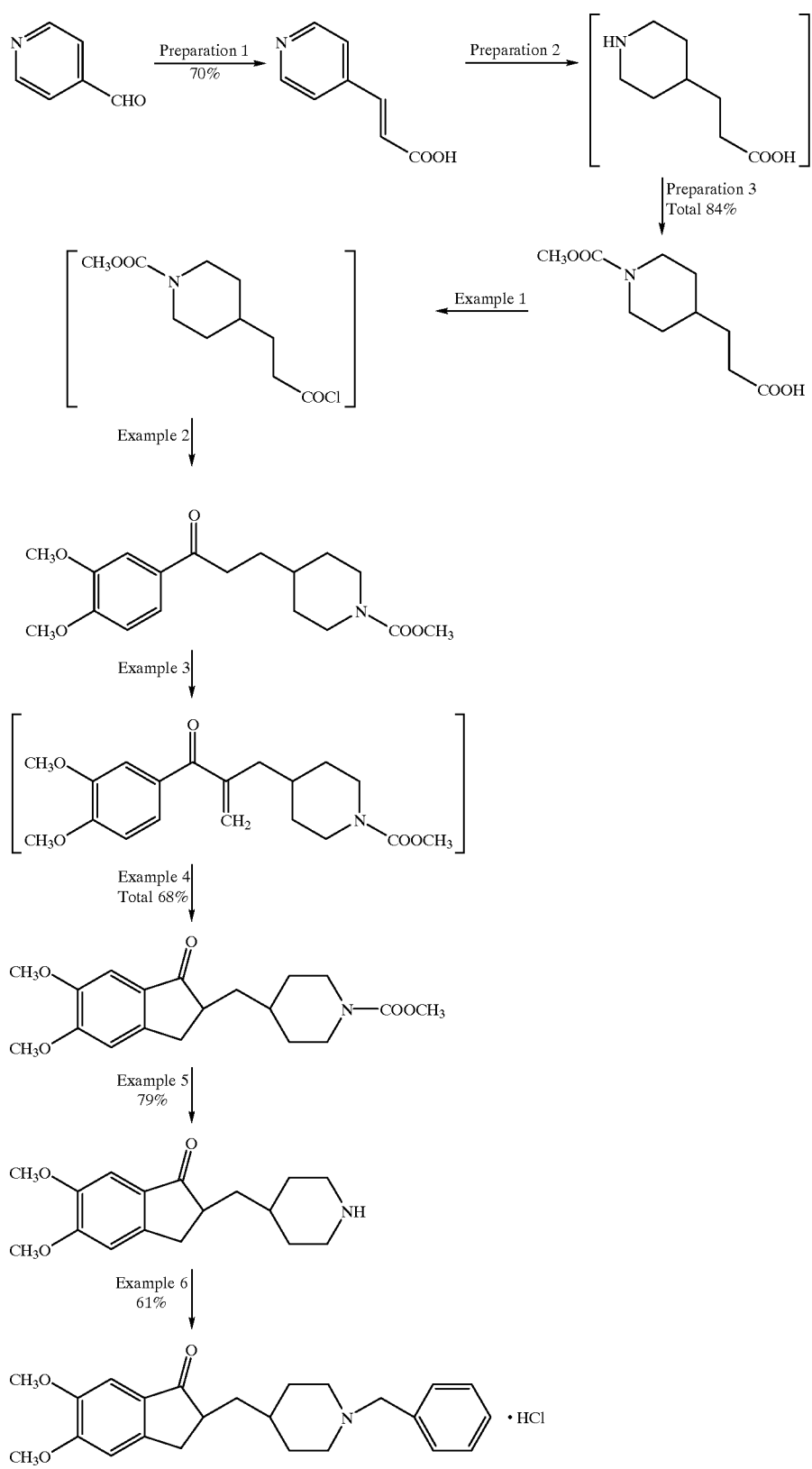

However, maximum total yield for Donepezil from the generally used starting material was 58.5% in JP-A 8-225527 (1996), next was 50.8% in JP-A 64-79151 (1989), and the lowest was 19.3% in WO97/22584. Therefore, it was not sufficient in either case as an industrial process.

Additionally, the maximum yield among all was the method of JP-A 8-225527(1996), however, yield of reduction in the last step was not reproducible, it, therefore, is assumed that the yield is inferior to JP-A 64-79151(1989) actually. (See Reference example described below.) Even the yield disclosed in this specification was correct, the total yield was not superior to Prior Arts (50.8%, a yeild throughout all the steps in JP-A64-79151(1989)), therefore, it did not show any superior effects.

Accordingly, there was no industrially or economically preferable process for Donepezil derivative having an excellent pharmacological action as prophylactic or medicament for senile dementia, especially for Alzheimer disease increasing the numbers of patients dramatically and having much social interest.

SUMMARY OF THE INVENTION

Regarding the foregoing problems, the present inventors have proceeded with extensive research. As a result, it has been found surprisingly that a reaction using a novel quaternary ammonium salt (I) affords 82.5% of total yield from a generally used material to Donepezil derivative, establishing the present invention.

Namely, the present invention provides an industrially preferable process for production of Donepezil and synthetic intermediates thereof.

The invention provides a process for producing a hydrogen halogenide salt of a Donepezil derivative (II) represented by the following formula;

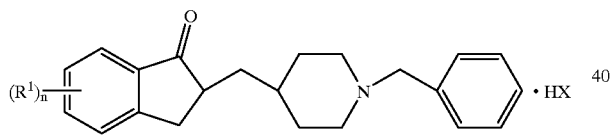

(II)

(wherein $R^1$, represents, the same as or different from each other, a hydrogen atom or a lower alkoxy group; n represents an integer of 1 to 4; and X represents a halogen atom.), comprising the step of reducing a quaternary ammonium salt (I) represented by the following formula;

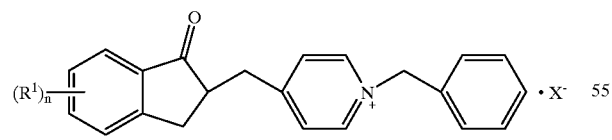

(I)

(Wherein $R^1$, n and X have the same meaning as defined above).

The invention provides a process for producing a Donepezil derivative from the salt (II) according to a conventional neutralization and then a process for producing a pharmacologically acceptable salt of the Donepezil derivative according to a conventional reaction to form such a salt.

The invention provides a quaternary ammonium salt (I) represented by the following formula;

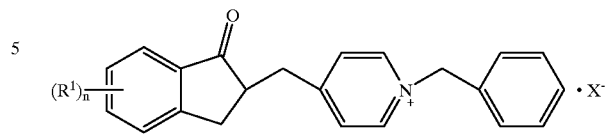

(I)

(Wherein $R^1$, n and X have the same meaning as defined in claim 1.).

Details for the present invention is one of the following processes for Donepezil.

(1) reduction of quaternary ammonium salt (I), (2) reaction of 2-(4-pyridyl)methyl-1-indanone derivative (III) with halogenated benzyl to obtain quaternary ammonium salt (I), then reduction of (I), (3) reaction of 2-alkoxycarbonyl-1-indanone derivative (IV) with halogenated (4-pyridyl)methyl (V) or a salt thereof and decarboxylation successively to obtain 2-(4-pyridyl)methyl-1-indanone derivative (III), then reaction of (III) with halogenated benzyl to obtain quaternary ammonium salt (I), then reduction of (I) or (4) reaction of 1-indanone derivative (VI) with carbonate ester (VII) to obtain 2-alkoxycarbonyl-1-indanone derivative (IV), followed by reaction of (IV) with halogenated (4-pyridyl)methyl (V) or a salt thereof and decarboxylation successively to obtain 2-(4-pyridyl) methyl-1-indanone derivative (III), then reaction of (III) with halogenated benzyl to obtain quaternary ammonium salt (I), then reduction of (I).

These processes are illustrated in the following chemical reaction scheme.

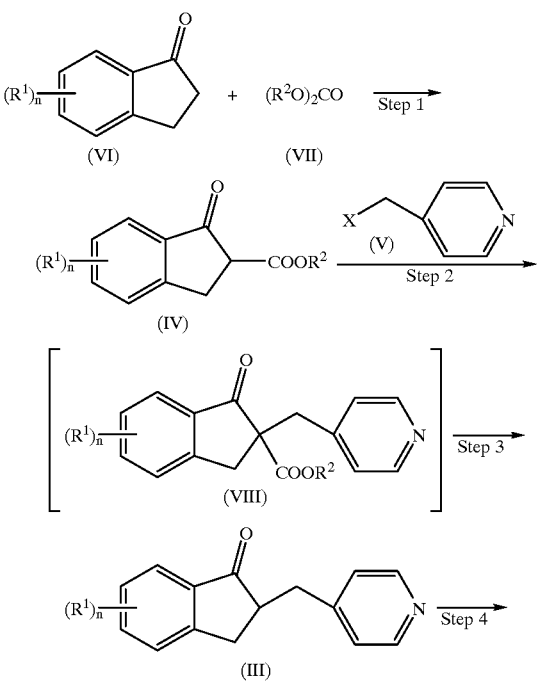

-continued

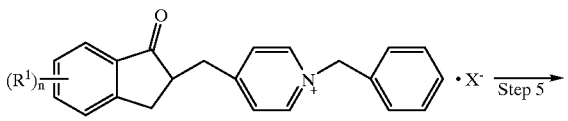

(I)

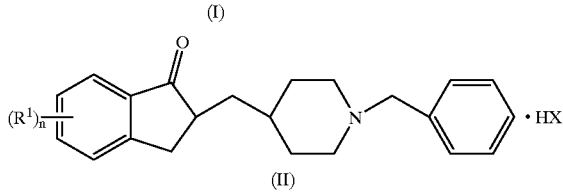

(II)

(Wherein R¹, R², n and X have the same meaning as defined above.)

Quaternary ammonium salt (I) in the present invention is represented by the following formula.

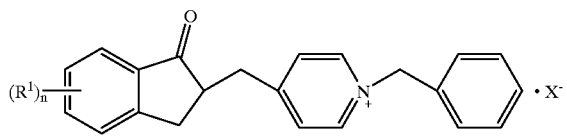
(I)

Wherein R¹ represents, same as or different from each other, a hydrogen atom or a lower alkoxy group, n represents an integer of 1 to 4 and X represents a halogen atom.

Lower alkoxy group herein means a straight or branched lower alkyl group having 1 to 6 carbon atoms bonded with oxygen atom, for example, methoxy, ethoxy, n-propoxy, i-propoxy, n-butoxy, i-butoxy, t-butoxy, pentyloxy or hexyloxy group. Among these, methoxy group, in particular 5, 6-dimethoxy, is preferable on the basis of pharmacological effect or safety for Donepezil derivative as a final compound.

Halogen atom herein represents bromine atom, chlorine atom, iodine atom or fluorine atom, and among them, bromine atom, chlorine atom or iodine atom affords preferable results.

Concrete examples for the quaternary ammonium salt (I) are in the following, however the invention is not limited to these examples only.

(1) 1-benzyl-4-(1-indanon-2-yl)methylpiridinium chloride,
(2) 1-benzyl-4-[(4-methoxy-1-indanon)-2-yl]methylpiridinium chloride,
(3) 1-benzyl-4-[(5-methoxy-1-indanon)-2-yl]methylpiridinium chloride,
(4) 1-benzyl-4-[(6-methoxy-1-indanon)-2-yl]methylpiridinium chloride,
(5) 1-benzyl-4-[(5,6-dimethoxy-1-indanon)-2-yl]methylpiridinium chloride,
(6) 1-benzyl-4-[(5,7-dimethoxy-1-indanon)-2-yl]methylpiridinium chloride,
(7) 1-benzyl-4-[(4,7-dimethoxy-1-indanon)-2-yl]methylpiridinium chloride,
(8) 1-benzyl-4-[(4,5-dimethoxy-1-indanon)-2-yl]methylpiridinium chloride,
(9) 1-benzyl-4-[(6,7-dimethoxy-1-indanon)-2-yl]methylpiridinium chloride,
(10) 1-benzyl-4-[(5,6,7-trimethoxy-1-indanon)-2-yl]methylpiridinium chloride,
(11) 1-benzyl-4-[(5,6-diethoxy-1-indanon)-2-yl]methylpiridinium chloride,
(12) 1-benzyl-4-(1-indanon2-yl)methylpiridinium bromide,
(13) 1-benzyl-4-[(4-methoxy-1-indanon)-2-yl]methylpiridinium bromide,
(14) 1-benzyl-4-[(5-methoxy-1-indanon)-2-yl]methylpiridinium bromide,
(15) 1-benzyl-4-[(6-methoxy-1-indanon)-2-yl]methylpiridinium bromide,
(16) 1-benzyl-4-[(5,6-dimethoxy-1-indanon)-2-yl]methylpiridinium bromide,
(17) 1-benzyl-4-[(5,7-dimethoxy-1-indanon)-2-yl]methylpiridinium bromide,
(18) 1-benzyl-4-[(4,7-dimethoxy-1-indanon)-2-yl]methylpiridinium bromide,
(19) 1-benzyl-4-[(4,5-dimethoxy-1-indanon)-2-yl]methylpiridinium bromide,
(20) 1-benzyl-4-[(6,7-dimethoxy-1-indanon)-2-yl]methylpiridinium bromide,
(21) 1-benzyl-4-[(5,6,7-trimethoxy-1-indanon)-2-yl]methylpiridinium bromide or
(22) 1-benzyl-4-[(5,6-diethoxy-1-indanon)-2-yl]methylpiridinium bromide.

Quaternary ammonium salt (I) in the present invention is a novel compound and is useful as a key intermediate to obtain the Donepezil derivative (II) in high yield.

Further, Donepezil derivative hydrogen halogenide salt (II) in the present invention is represented by the following formula.

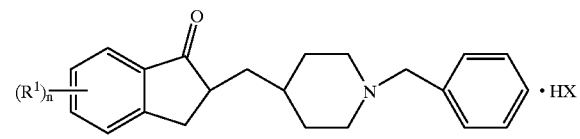
(II)

Wherein R¹, n and X have the same meaning as defined above.

Concrete examples for the Donepezil derivative hydrogen halogenide salts (II) are the hydrogen halogenide salt of the following, however the invention is not limited to these examples only.

(1) 1-benzyl-4-(1-indanon-2-yl)methylpiperidine,
(2) 1-benzyl-4-[(4-methoxy-1-indanon)-2-yl]methylpiperidine,
(3) 1-benzyl-4-[(5-methoxy-1-indanon)-2-yl]methylpiperidine,
(4) 1-benzyl-4-[(6-methoxy-1-indanon)-2-yl]methylpiperidine,
(5) 1-benzyl-4-[(5,6-dimethoxy-1-indanon)-2-yl]methylpiperidine,
(6) 1-benzyl-4-[(5,7-dimethoxy-1-indanon)-2-yl]methylpiperidine,
(7) 1-benzyl-4-[(4,7-dimethoxy-1-indanon)-2-yl]methylpiperidine,
(8) 1-benzyl-4-[(4,5-dimethoxy-1-indanon)-2-yl]methylpiperidine,
(9) 1-benzyl-4-[(6,7-dimethoxy-1-indanon)-2-yl]methylpiperidine,
(10) 1-benzyl-4-[(5,6,7-trimethoxy-1-indanon)-2-yl]methylpiperidine or
(11) 1-benzyl-4-[(5,6-diethoxy-1-indanon)-2-yl]methylpiperidine.

When necessary, Donepezil derivative hydrogen halogenide salt (II) in the present invention can be converted to a optional pharmaceutically acceptable salt thereof by a usual manner (salt exchange), e.g., neutralization with base followed by treatment with acid, or treatment with excess acid. Kind of the salt is not limited either, however, hydrochloride is preferable.

Further, 2-(4-pyridyl)methyl-1-indanone derivative (III) in the present invention is represented by the following formula.

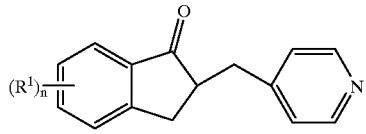
(III)

Wherein $R^1$ and n have the same meaning as defined above.

Concrete examples for the 2-(4-pyridyl)methyl-1-indanone derivative (III) are in the following, however the invention is not limited to these examples only.
(1) 2-(4-pyridyl)methyl-1-indanone,
(2) 2-(4-pyridyl)methyl-4-methoxy-1-indanone,
(3) 2-(4-pyridyl)methyl-5-methoxy-1-indanone,
(4) 2-(4-pyridyl)methyl-6-methoxy-1-indanone,
(5) 2-(4-pyridyl)methyl-5,6-dimethoxy-1-indanone,
(6) 2-(4-pyridyl)methyl-5,7-dimethoxy-1-indanone,
(7) 2-(4-pyridyl)methyl-4,7-dimethoxy-1-indanone,
(8) 2-(4-pyridyl)methyl-4,5-dimethoxy-1-indanone,
(9) 2-(4-pyridyl)methyl-6,7-dimethoxy-1-indanone,
(10) 2-(4-pyridyl)methyl-5,6,7-trimethoxy-1-indanone or
(11) 2-(4-pyridyl)methyl-5,6-diethoxy-1-indanone.

These are known compounds, and can be produced according to the procedure disclosed in J. Heterocyclic Chem.,2(4),366-70(1965). (total yield=48.4%(55%×88%)) for example, however, can be produced in much higher yield according to the present invention (total yield=82.5%(98%×85%×100%×99%)).

Further, 2-alkoxycarbonyl-1-indanone derivative (IV) in the present invention is represented by the following formula.

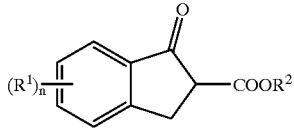
(IV)

Wherein $R^2$ represents a lower alkyl group, $R^1$ and n have the same meaning as defined above.

Lower alkyl group herein means a straight or branched alkyl group having 1 to 6 carbon atoms, for example, methyl, ethyl, n-propyl, i-propyl, n-butyl, i-butyl, t-butyl, pentyl or hexyl group. Among these, methyl, ethyl or propyl group is preferable.

Concrete examples for the 2-alkoxycarbonyl-1-indanone derivative (IV) are in the following, however the invention is not limited to these examples only.
(1) 2-methoxycarbonyl-1-indanone,
(2) 2-methoxycarbonyl-4-methoxy-1-indanone,
(3) 2-methoxycarbonyl-5-methoxy-1-indanone,
(4) 2-methoxycarbonyl-6-methoxyl-indanone,
(5) 2-methoxycarbonyl-5,6-dimethoxy-1-indanone,
(6) 2-methoxycarbonyl-5,7-dimethoxy-1-indanone,
(7) 2-methoxycarbonyl-4,7-dimethoxy-1-indanone,
(8) 2-methoxycarbonyl-4,5-dimethoxy-1-indanone,
(9) 2-methoxycarbonyl-6,7-dimethoxy-1-indanone,
(10) 2-methoxycarbonyl-5,6,7-trimethoxy-1-indanone,
(11) 2-methoxycarbonyl-5,6-diethoxy-1-indanone,
(12) 2-ethoxycarbonyl-1-indanone,
(13) 2-ethoxycarbonyl-4-methoxy-1-indanone,
(14) 2-ethoxycarbonyl-5-methoxy-1-indanone,
(15) 2-ethoxycarbonyl-6-methoxy-1-indanone,
(16) 2-ethoxycarbonyl-5,6-dimethoxy-1-indanone,
(17) 2-ethoxycarbonyl-5,7-dimethoxy-1-indanone,
(18) 2-ethoxycarbonyl-4,7-dimethoxy-1-indanone,
(19) 2-ethoxycarbonyl-4,5-dimethoxy-1-indanone,
(20) 2-ethoxycarbonyl-6,7-dimethoxy-1-indanone,
(21) 2-ethoxycarbonyl-5,6,7-trimethoxy-1-indanone or
(22) 2-ethoxycarbonyl-5,6-diethoxy-1-indanone.

These are known compounds also, and can be produced quantitatively according to the procedure disclosed in Example 9-A1 of EP-534,859 (yield=98%).

Further, halogenated (4-pyridyl)methyl derivative (V) in the present invention is represented by the following formula.
(Wherein X represents a halogen atom.)

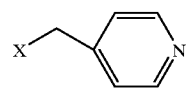
(V)

Concrete examples for the halogenated (4-pyridyl)methyl derivative (V) are in the following. They can be salt.
(1) (4-pyridyl)methyl chloride,
(2) (4-pyridyl)methyl bromide or
(3) (4-pyridyl)methyl iodide.

They are known compounds, and are available as reagents or industrial bulk materials generally.

Further, 1-indanone derivative (VI) in the present invention is represented by the following formula. (Wherein $R^1$ and n have the same meaning as defined above.)

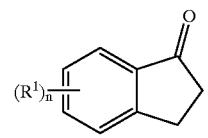
(VI)

Concrete examples for the 1-indanone derivative (VI) are in the following.
(1) 1-indanone,
(2) 4-methoxy-1-indanone,
(3) 5-methoxy-1-indanone,
(4) 6-methoxy-1-indanone,
(5) 5,6-dimethoxy-1-indanone,
(6) 5,7-dimethoxy-1-indanone,
(7) 4,7-dimethoxy-1-indanone,
(8) 4,5-dimethoxy-1-indanone,
(9) 6,7-dimethoxy-1-indanone,
(10) 5,6,7-trimethoxy-1-indanone or
(11) 5,6-diethoxy-1-indanone.

They are known compounds also, and are available as reagents or industrial bulk materials generally.

Finally, carbonate ester (VII) in the present invention is represented by the formula $(R^2O)_2CO$. (Wherein $R^2$ have the same meaning as defined above.)

Concrete examples for the carbonate ester (VII) are in the following.
(1) dimethyl carbonate,
(2) diethyl carbonate, (3) dipropyl carbonate or
(4) methylethyl carbonate.

They are known compounds also, and are available as reagents or industrial bulk materials generally.

Detailed processes for the present invention are as follows. (See the foregoing chemical reaction formulae.) (1) Step 1

Reaction of 1-indanone derivative (VI) with carbonate ester (VII) to obtain 2-alkoxycarbonyl-1-indanone derivative (IV) comprises this step according to the procedure of Example 9-A1in EP-534,859, the procedure in Chem. Pharm. Bull.42(3),541–550(1994) or the procedure in Tetrahedron,30, 507–512, 1974. Among them, Example 9-A1in EP-534,859 affords the highest yield and producible quantitatively. (2) Step 2

Reaction of 2-alkoxycarbonyl-1-indanone derivative (IV) with halogenated (4-pyridyl)methyl derivative (V) or a salt thereof to obtain 2-alkoxycarbonyl-2-(4-pyridyl)methyl-1-indanone derivative (VIII) comprises this step.

This step can be done in the presence of base according to a usual manner.

In the non-aqueous system, base is not limited though, for example, sodium hydride, sodium, sodium amide, lithium diisopropylamide (LDA), lithium hexamethyldisilazane (LHMDS), sodium methoxide, sodium ethoxide or potassium t-butoxide can be used. Solvent in this step is not limited either, for example, DMF, THF, DMSO, dioxane, HMPA, HMPT or mixed solvents can be used.

Moreover, this step can be done in aqueous system also in the presence of phase transfer catalyst and base. Phase transfer catalyst herein is not limited though, they are quaternary ammonium salt, quaternary phosphonium salt or sulfonium salt generally.

Concrete examples for the quaternary ammonium salt are tetramethylammonium iodide, tetraehylammonium iodide, tetrapropylammonium iodide, tetrabutylammonium iodide, tetrapentylammonium iodide, tetrahexylammonium iodide, tetraheptylammonium iodide, tetraoctylammonium iodide, tetrahexadecylammonium iodide, tetraoctadecylammonium iodide, benzyltrimethylammonium bromide, benzyltriethylammonium bromide, benzyltributylammonium bromide, 1-methylpiridinium iodide, 1-hexadecylpiridinium iodide, 1,4-diethylpiridinium iodide, teramethyl-2-butylammonium chloride, trimethylcyclopropylammonium chloride, tetrabutylammonium bromide, tetraoctylammonium bromide, t-butylethyldimethylammonium bromide, tetradecyltrimethylammonium bromide, hexadecyltrimethylammonium bromide or octadecyltrimethylammonium bromide.

Additionally, concrete examples for the quaternary phosphonium salt are tributylmethylphosphonium iodide, triethylmethylphosphonium iodide, methyltriphenoxyphosphonium iodide, butyltriphenylphosphonium iodide, tetrabutylphosphonium bromide, benzyltriphenylphosphonium bromide, hexadecyltrimethylphosphonium bromide, hexadecyltributylphosphonium bromide, hexadecyldimethylphosphonium bromide or tetraphenylphosphonium chloride.

Further, concrete examples for the sulfonium salt are dibutylmethylsulfonium iodide, trimethylsulfonium iodide or triethylsulfonium iodide.

These phase transfer catalysts are available as reagents or industrial bulk materials generally.

Finally, in the aqueous system, base is not limited either, concrete examples are sodium hydroxide, potassium hydroxide or barium hydroxide.

Solvent in this step is not limited either, for example, water, water/toluene, water/benzene, water/xylene, water/halogenated hydrocarbon in particular a chlorinated hydrocarbon such as methylene chloride, chloroform, carbontetrachloride, etc. or mixed solvents can be used. (3) Step 3

Decarboxylation of 2-alkoxycarbonyl-2-(4-pyridyl)methyl-1-indanone derivative (VIII) to obtain 2-(4-pyridyl)methyl-1-indanone derivative (III) comprises this step.

This step can be done in the presence of base according to a usual decarboxylation manner. Base is not limited either in this step, for example, potassium hydroxide, sodium hydroxide or barium hydroxide can be used.

Solvent in this step is not limited either, for example, lower alcohol such as ethanol, methanol or propanol, THF, DMF, DMSO, dioxane or mixed solvents can be used.

As another procedure for this step, decarboxylation can be done according to the manner disclosed in Tetrahedron Lett., 957, 1973., in water/DMSO in the presence of sodium chloride. (4) Step 4

Reaction of 2-(4-pyridyl)methyl-1-indanone derivative (III) with halogenated benzyl to obtain quaternary ammonium salt (I) comprises this step.

This step can be done according to a usual manner to prepare quaternary ammonium salt. Examples for the halogenated benzyl are benzyl bromide or benzyl chloride. As solvent, acetonitrile, THF, DMF, DMSO, dioxane, 1,2-dimethoxyethane, ether, lower alcohol, acetone, MEK (2-butanone), MIBK (methylisobutylketone), N-methylpyrrolidone or mixed solvents can be used. (5) Step 5

Reduction of quaternary ammonium salt (I) to obtain the Donepezil derivative hydrogenhalogenide salt (II) as the final compound in the present invention comprises this step. Reduction procedure is not limited either, it is done by catalytic reduction in the presence of catalyst usually.

Concrete examples for the catalyst are platinum compound such as platinum oxide, palladium compound such as palladium/carbon, nickel compound such as Raney nickel, ruthenium compound such as ruthenium oxide. As solvent, water, lower alcohol such as ethanol or methanol, THF, DMF, DMSO, dioxane, N-methylpyrrolidone, halogenated hydrocarbon in particular a chlorinated hydrocarbon such as methylene chloride, chloroform, carbontetrachloride, etc., acetone, MEK, MIBK, acetonitrile, ethyl acetate, benzene, toluene, xylene or mixed solvents can be used.

Reaction condition in this step is not limited either, it will complete within several hours at room temperature and under atmosphere pressure.

Obtained Donepezil derivative hydrogen halogenide salt (II) can be lead to a free base orapharmacologically acceptable salt thereof according to a usual manner.

EXAMPLES

The present invention will now be described in more detail with reference to the following examples. It is needless to say that the technical scope of the present invention is not limited to these examples.

Example 1

Synthesis of 5,6-dimethoxy-2-(4-pyridyl)methyl-1-indanone

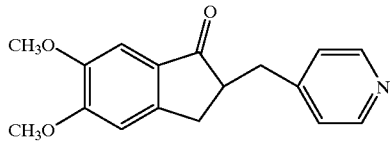

2.00 g (7.57 mmol) of 5,6-dimethoxy-2-ethoxycarbonyl-1-indanone synthesized according to the Example 9-A1of EP-534, 859 was dissolved in 40 ml of DMF (dimethylformamide), then 0.73 g (18.3 mmol) of a dispersion of 60% sodium hydride in oil was added under cooling in iced water bath, then stirring was kept for 30 minutes at room temperature. It was cooled in iced water bath again, 1.49 g (18.3 mmol) of 4-pyridiylmethyl chloride (4-picolyl chloride) was added hereinto, and stirring was kept for 30 minutes under the same condition. Further stirring was kept overnight at room temperature. Under cooling in iced water bath, 200 ml of water was added hereinto, followed by extraction with 200 ml of ethyl acetate. The organic layer was washed with 200 ml of saturated brine twice, and dried with $MgSO_4$, then concentration under reduced pressure afforded 3.40 g of dark brown oil.

This oil was dissolved in 50 ml of ethanol, then 10 ml of water and 1.99 g (30.3 mmol) of 85.5% -potassium hydroxide were added hereinto, and was heated under reflux for 30 minutes. The reaction mixture was cooled to room temperature, and was concentrated under reduced pressure, then 50 ml of water was added. Filtration of the precipitated crystal and drying afforded 1.82 g of the pale brown crystalline title compound.

(Yield: 85% through 2 steps) melting point: 192–193° C. (literature: 190–191° C. (J. Heterocyclic Chem.,2(4),366-70, 1965.)). $^1$H-NMR(400 MHz, $CDCl_3$)δ (ppm) 2.66–2.74(2H, m), 2.96–3.04(1H,m), 3.12(1H,dd,J=7.6 Hz,J=16. 8Hz), 3.35(1H,dd,J=4.4 Hz,J=14 Hz), 3.92(3H,s), 3.95(3H,s), 6.82 (1H,s) 7.18(2H,d,J=6 Hz), 7.20(1H,s), 8.51(2H,d,J=6 Hz). ESI-MS: m/z=284 (M+H)+.

Example 2

Synthesis of 1-benzyl-4-[(5,6-dimethoxy-1-indanon)-2-yl]methylpyridinium bromide

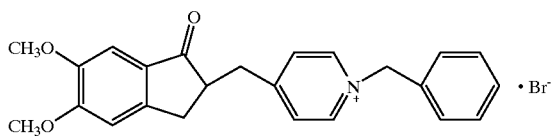

1.00 g (3.53 mmol) of 5,6-dimethoxy-2-(4-pyridyl) methyl-1-indanone was dissolved in 30 ml of acetonitrile under reflux condition, 0.50 ml (4.21 mmol) of benzyl bromide was added hereinto. After keeping heating under reflux for 2.5 hours, reaction mixture was cooled to room temperature, followed by concentration under reduced pressure. 50 ml of n-hexane was added to the residue. Filtration of the precipitated crystal and drying afforded 1.60 g of the pale yellow crystalline title compound.

(Yield: quantitatively) melting point: 173–177° C. $^1$H-NMR(400 MHz,DMSO-$d_6$) δ(ppm) 2.70(1H,dd,J=3.6 Hz,J=16.4 Hz), 3.01(1H,dd,J=9.2 Hz,J=14 Hz), 3.12(1H,dd, J=7.6Hz,J=16.4Hz), 3.16–3.24(1H,m),3.30–3.98(1H,m), 3.77(3H,s), 3.83(3H,s), 5.81(2H,s), 7.06(1H,s), 7.07(1H,s), 7.38–7.48(3H,m), 7.50–7.56(2H,m), 8.13(2H,d,J=6.4 Hz), 9.14(2H,d,J=6.4 Hz). ESI-MS: m/z=374 (M−Br)+.

Example 3

Synthesis of 1-benzyl-4-[(5,6-dimethoxy-1-indanon)-2-yl]methylpiperidine hydrochloride (Donepezil Hydrochloride)

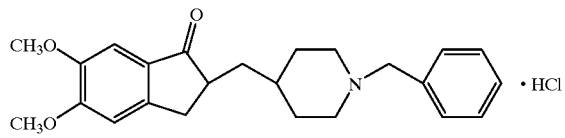

1.00 g (2.20 mmol) of 1-benzyl-4-[(5,6-dimethoxy-1-indanon) -2-yl]methylpyridinium bromide was dissolved in 15 ml of methanol. Hydrogenation in the presence of 0.1 g of platinum oxide (IV) was done for 3 hours at room temperature under atmosphere pressure. After the catalyst was filtered off, filtrate was concentrated under reduced pressure, 30 ml of saturated sodium carbonate aqueous solution was added hereinto, followed by extraction with 50 ml of ethyl acetate thrice. After drying with $MgSO_4$, concentration under reduced pressure afforded 0.83 g of Donepezil free base.

(Yield: 99% ) $^1$H-NMR(400 MHz,$CDCl_3$) δ (ppm) 1.27–1.42(3H,m), 1.42–1.55(1H,m), 1.63–1.77(2H,m), 1.87–2.03(3H,m) 2.66–2.74(2H,m), 2.86–2.94(2H,m), 3.23 (1H,dd,J=8 Hz,J=17.6 Hz), 3.50(2H,s), 3.90(3H,s), 3.96(3H, s), 6.85(1H,s),7.17(1H,s), 7.22–7.33(5H,m).

This was lead to hydrochloride according to a usual manner, and recrystallizaion from ethanol/isopropylether afforded 0.83 g of the white crystalline title compound. (Yield: 91% through 2 steps) melting point: 211–212° C. (Decomposition) (literature: 211–212° C. (Decomposition), (Example 4 of JP-A 64-79151(1989)).

$^1$H-NMR(400 MHz, $CDCl_3$) δ (ppm) 1.48–1.58(1H,m), 1.76–1.90(2H,m), 1.90–2.02(1H,m), 2.02–2.20(3H,m), 2.60–2.76(4H,m), 3.29(1H,dd,J=7.6 Hz,J=17.2 Hz), 3.41–3.54(2H,m), 3.90(3H,s), 3.96(3H,s), 4.12–4.22(2H,m) 6.85(1H,s), 7.12(1H,s), 7.42–7.48(3H,m), 7.64(2H,br–s), 12.25–12.45(1H,m). ESI-MS: m/z=380 (M+H)+.

Reference Example 1

Synthesis of Donepezil (free base) (Reproduction experiment result of the Example 6 in JP-A 8-225,527 (1996))

50 ml of methanol and 1 g of platinum oxide (IV) were added to 10.0 g (22.1 mmol) of 5,6-dimethoxy-2-(4-pyridyl) methyleneindan-1-one synthesized according to the Example 4 in JP-A 8-225,527(1996). Hydrogenation was done for 24 hours at room temperature under atmosphere pressure. After the catalyst was filtered off, filtrate was concentrated under reduced pressure, 200 ml of 5% -sodium carbonate aqueous solution was added hereinto, followed by extraction with 150 ml and 100 ml twice of methylene chloride. After drying with $MgSO_4$, concentration under reduced pressure afforded 9.1 g of black oil. TLC (methanol/ methylene chloride) analysis of this black oil showed many by-product spots. Purification of this oil by (NH) silicagelcolumnchromatography (n-hexane/ethyl acetate) afforded 3.2 g of the white crystalline title compound. (Yield: 38%, literature: 81%, (Example 6 in JP-A 8-225,527 (1996))

What is claimed is:

1. A process for producing a hydrogen halogenide salt of a Donepezil derivative (II) represented by the following formula;

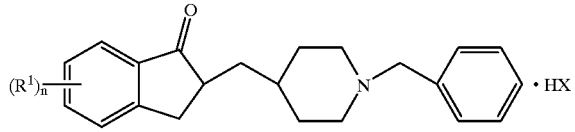

(II)

(wherein $R^1$ represents, the same as or different from each other, a hydrogen atom or a lower alkoxy group; n represents an integer of 1 to 4; and X represents a halogen atom.), comprising the step of reducing a quaternary ammonium salt (I) represented by the following formula;

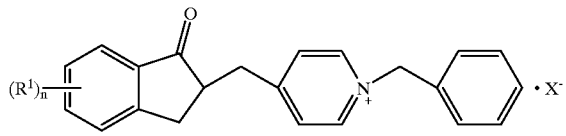

(I)

(Wherein $R^1$, n and X have the same meaning as defined above).

2. The process as claimed in claim 1, in which the quaternary ammonium salt (I) is produced by reacting 2-(4-pyridyl) methyl-1-indanone derivative (III) represented by the following formula;

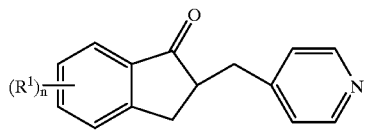

(III)

(Wherein $R^1$ and n have the same meaning as defined above.) with a halogenated benzyl.

3. The process as claimed in claim 2, in which 2-(4-pyridyl) methyl-1-indanone derivative (III) is produced by reacting 2-alkoxycarbonyl-1-indanone derivative (IV) represented by the following formula;

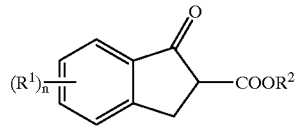

(IV)

(Wherein $R^2$ represents a lower alkyl group, $R^1$ and n have the same meaning as defined above.) with a halogenated (4-pyridyl)methyl (V) represented by the following formula or a salt thereof;

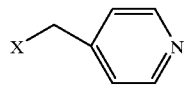

(V)

(Wherein X represents a halogen atom.) and decarboxylating the reaction product.

4. The process as claimed in claim 3, in which a 2-alkoxycarbonyl-1-indanone derivative (IV) is produced by reacting a 1-indanone derivative (VI) represented by the following formula;

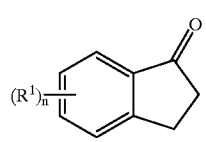

(VI)

(Wherein $R^1$ and n have the same meaning as defined above.) with carbonate ester (VII) represented by $(R^2O)_2CO$;

(Wherein $R^2$ has the same meaning as defined above.).

5. The process as claimed in claim 1, in which the reduction is catalytic reduction in the presence of platinum oxide, palladium/carbon, Raney nickel or ruthenium oxide.

6. The process as claimed in claim 1, in which the halogen atom for X of the quaternary ammonium salt (I) is bromine atom, chlorine atom or iodine atom.

7. The process as claimed in claim 3, in which the halogenated (4-pyridyl)methyl (V) is (4-pyridyl)methyl chloride, (4-pyridyl) methyl bromide or (4-pyridyl)methyl iodide.

8. The process as claimed in claim 4, in which the carbonate ester (VI) is dimethyl carbonate, diethyl carbonate, dipropyl carbonate or methylethyl carbonate.

9. The process as claimed in claim 1, in which the salt is that of hydrochloride, hydrobromide or hydroiodide; n being 2; and $R^1$ being methoxy, attached to 5- and 6- positions.

10. A quaternary ammonium salt (I) represented by the following formula;

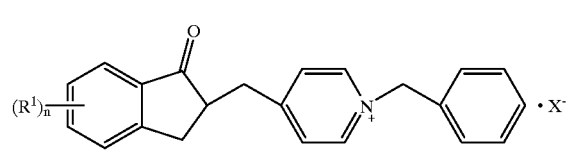

(I)

(Wherein $R^1$, n and X have the same meaning as defined in claim 1.).

* * * * *